Nov. 10, 1953 A. KREBS Plant Pat. 1,226
ROSE PLANT
Filed Jan. 17, 1949
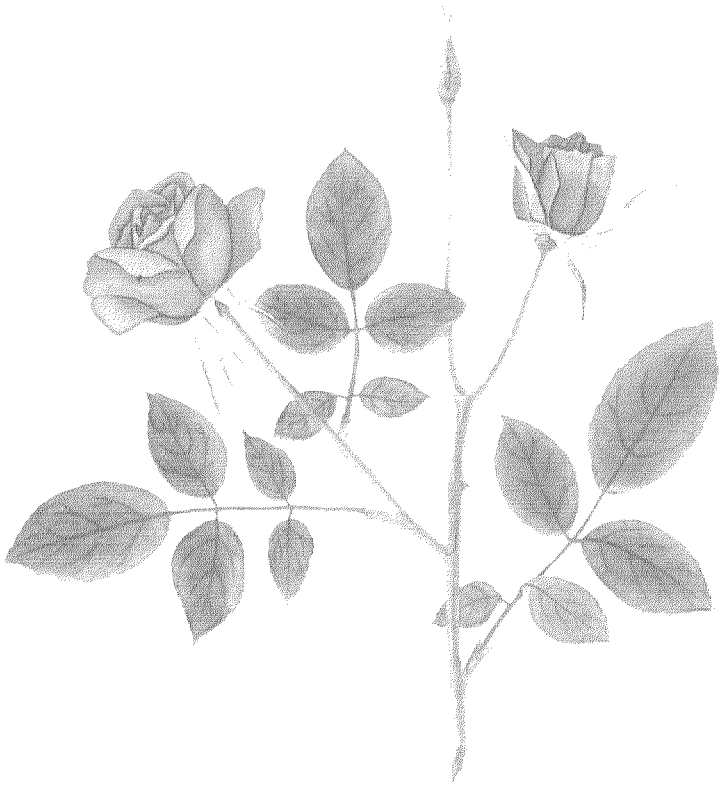
INVENTOR.
BY Alfred Krebs
Lyon & Lyon
ATTORNEYS Patented Nov. 10, 1953

Plant Pat. 1,226

UNITED STATES PATENT OFFICE 1,226

ROSE PLANT

Alfred Krebs, Montebello, Calif., assignor of one-half to Edward E. Marsh, Pasadena, Calif.

Application January 17, 1949, Serial No. 71,347

1 Claim. (Cl. 47—61)

This invention relates to a new and distinctive variety of rose plant which has as its parentage the Cecile Brunner crossed with an unknown variety of rose. The rose was produced through cross-pollenization of the Cecile Brunner and an unknown rose, and the cross-pollenization was carried out at Montebello, California. The plant has been reproduced by budding at Montebello, California.

The new and distinctive variety of rose embracing this variety is characterized by the following:

1. *Color.*—Generally designated as scarlet red approaching, however, the magenta of Plate 27, shading to Plate 27/2 of the color charts of the Royal Horticultural Society issued by the British Colour Council, or rose red of the same charts.

2. The shape of the bud is very pointed and the bloom or rose of the plant is a medium star-shaped double bloom having somewhat the characteristics of the Cecile Brunner bud in size and being rather tightly closed, having the characteristic Cecile Brunner long sepals and as the bud opens the bloom is of cup shape. The rose in full bloom is of multiple petal rather closely set and of irregular pattern.

3. The rose is only of slight fragrance.

4. The rose plant is further characterized as being of abundant bloom and being a substantially continuous bloomer, and is vigorous.

5. The rose plant is further characterized by its upright growth and its abundant small glossy foliage which is a parsley green shading from its darker green color comparable with the chart 00962/2 to its lighter shade of 00962/3 of the color charts of the Royal Horticultural Society.

The drawing illustrates the bloom as it is open, in its cup shape, and to a position of rather mature opening; also, the foliage and a bud.

Further detailed description is given below.

The rose plant of this invention is of the bush type as distinguished from a climber. During its stage of development from a bud to a fully opened rose there is very little change in color of the bloom, the variation being from the bud to its full open condition of a shading from the darker magenta of Plate 27 through Plate 27/1 to Plate 27/2 of the color charts of the Royal Horticultural Society issued by the British Colour Council, or from rose red to China rose of the same charts. This is a particular characteristic of this rose in that there is very little fading of color intensity from the bud to the fully opened bloom.

This rose plant is of the hardy, tall, bushy, outdoor, seeding, garden decoration type, and is in the polyantha class.

The flower, which has a slight, spicy fragrance, is produced in abundance outdoors in Pasadena, California. There are several flowers to a stem, which is normally long, and they are in irregular clusters, and their blooming is continuous.

The bud has a short peduncle which is slender, bending, medium reddish green in color and entirely smooth in texture.

Before the calyx breaks the bud is small and long pointed with foliaceous appendages and with slender foliaceous parts extending ¾ or more of its length.

As the calyx breaks the color is ruby red, 827. This and color references hereinafter are to the chart of the Royal Horticultural Society.

As the first petal opens, which it does well, it is very small and very pointed, and has an outside color of rose red, 724, and an inside color of rose red, 724. The bloom size is small—2 to 2½ inches, with double petals, irregularly arranged, cupped at first and rolled outward, becoming very loosely rolled outward at maturity.

The petals are soft and are satiny both inside and outside, are striped in color and are obovate on the outside of the flower, obovate intermediate and obovate inside.

A newly opened flower grown outdoors in Pasadena, California, in June 1952, had the following coloring: the outside surface of the outside petal was rose red 724, the inside surface was rose red 724; the outside surface of the intermediate petal was rose red 724, the inside surface was rose red 724; the outside surface of the inner petal was rose red 724, the inside surface was rose red 724.

A flower open for three days outdoors in Pasadena, California, in June 1952, showed the following: the outside surface of the outside petal was China rose 024/1 in color, the inside surface was China rose 024 in color; the outside surface of the inner petal was China rose 024/1 in color, and the inside surface was rose red 724/3 in color. The general color effect when the flower was newly opened was rose red; after three days it was China rose. The longevity of the flower generally is 4 days when kept on a bush in a garden, in June, and 1 day at living room temperature in June.

There are reproductive organs, such as: the stamens, which are few in number, irregular and mixed with petaloids; the filaments, which are long, white and most with anthers; the anthers, which are medium in size, brown in color and open at various times; the pollen, which is very sparse; the pistils, of which there are very few; the styles, which are even, medium in length, medium in texture, and loosely separated; the stigma, which is yellow in color; the ovaries, which are all enclosed; the hips, which are ovoid in shape, green in color, smooth in texture and thin; the sepals, which are permanent, very long and straight; and the seeds, which are very few in number.

The leaves of the plant generally have 5 leaflets, are normal in number, medium in size and moderately thin.

The leaflets are oval shape with acute apex, acute base and simply serrated margin.

The color of the leaves when young is, upper surface, moderately red, under surface, moderately red; when mature the color of the under surface is light green, the upper surface, normal green.

The rachis is medium in weight, the upper side is grooved and hairy and the under side is sparsely hairy.

The stipules are moderately long and moderately wide with short points turning out at an angle of less than 45°.

The growth of the plant is vigorous, bushy and much branched. The canes are medium in weight, and the main stems are green in color, with few thorns, medium in length and hooked downward, no prickles and no hairs.

The branches are dull red in color, with a few thorns, which are medium in length and hooked downward with long narrow base, no prickles and no hairs.

New shoots are dull red in color, with no thorns, no prickles and no hairs.

I claim:

The new and distinct variety of bush rose plant as described and illustrated, characterized by its small bloom, its substantial constancy of magenta color from bud to full open bloom, and further characterized by its extremely vigorous growth and its abundant continuous blooming, and having as its parentage a Cecile Brunner rose crossed with an unknown variety of rose plant.

ALFRED KREBS.

No references cited.